(12) United States Patent
Su et al.

(10) Patent No.: US 12,409,201 B2
(45) Date of Patent: Sep. 9, 2025

(54) CARE COMPOSITION AND USE THEREOF

(71) Applicant: Jane-Yi Su, Taipei (TW)

(72) Inventors: Jane-Yi Su, Taipei (TW); Chin-Wen Chi, Taipei (TW)

(73) Assignee: Jane-Yi Su, Taipei (TW)

( * ) Notice: Subject to any disclaimer, the term of this patent is extended or adjusted under 35 U.S.C. 154(b) by 403 days.

(21) Appl. No.: 17/496,056

(22) Filed: Oct. 7, 2021

(65) Prior Publication Data

US 2022/0110995 A1    Apr. 14, 2022

(30) Foreign Application Priority Data

Oct. 8, 2020 (TW) ................................ 109135028

(51) Int. Cl.
| | | |
|---|---|---|
| *A61K 36/39* | (2006.01) | |
| *A61K 9/00* | (2006.01) | |
| *A61K 9/08* | (2006.01) | |
| *A61K 33/00* | (2006.01) | |
| *A61K 33/06* | (2006.01) | |
| *A61K 36/48* | (2006.01) | |
| *A61K 36/8945* | (2006.01) | |
| *A61K 45/06* | (2006.01) | |
| *A61K 47/02* | (2006.01) | |
| *A61P 11/06* | (2006.01) | |
| *A61P 11/12* | (2006.01) | |
| *A61P 29/00* | (2006.01) | |
| *A61P 37/02* | (2006.01) | |
| *A61P 37/06* | (2006.01) | |
| *A61P 37/08* | (2006.01) | |

(52) U.S. Cl.
CPC ............ *A61K 36/39* (2013.01); *A61K 9/0073* (2013.01); *A61K 9/08* (2013.01); *A61K 33/00* (2013.01); *A61K 33/06* (2013.01); *A61K 36/48* (2013.01); *A61K 36/8945* (2013.01); *A61K 45/06* (2013.01); *A61K 47/02* (2013.01); *A61P 11/06* (2018.01); *A61P 11/12* (2018.01); *A61P 29/00* (2018.01); *A61P 37/02* (2018.01); *A61P 37/06* (2018.01); *A61P 37/08* (2018.01); *A61K 2236/00* (2013.01); *A61K 2236/15* (2013.01); *A61K 2236/17* (2013.01); *A61K 2236/37* (2013.01); *A61K 2236/53* (2013.01)

(58) Field of Classification Search
None
See application file for complete search history.

(56) References Cited

FOREIGN PATENT DOCUMENTS

| CN | 102210737 A | * | 10/2011 | |
|---|---|---|---|---|
| CN | 108498560 A | * | 9/2018 | ............. A61K 36/39 |

OTHER PUBLICATIONS

English translation for CN102210737A (2011).*
"Marvels of Mucus and Phlegm The Slim That Keeps You Healthy", NIH News in Health (Aug. 2020), an internet article (p. 1-4) obtained from the website: https://newsinhealth.nih.gov/sites/newsinhealth/files/2020/August/NIHNiHAug2020.pdf (Year: 2020).*
Bastier et al ("Nasal irrigation: From empiricism to evidence-based medicine. A review", European Annals of Otorhinolaryngology, Head and Neck Diseases, vol. 132 (issue 5) (Nov. 2015), p. 281-285) (Year: 2015).*
Lee et al ("Purple Sweet Potato Leaf Extract Induces Apoptosis and Reduces Inflammatory Adipokine Expression in 3T3-L1 Differentiated Adipocytes", Evidence-Based Complementary and Alternative Medicine, vol. 2015, Article ID 126302, 9 pages) (Year: 2015).*
English translation for CN 108498560 A (Year: 2018).*

* cited by examiner

*Primary Examiner* — Sin J Lee
(74) *Attorney, Agent, or Firm* — MUNCY, GEISSLER, OLDS & LOWE, P.C.

(57) ABSTRACT

A care composition includes an extract from the stems and/or the leaves of a sweet potato, and/or a yam-bean, and/or a yam together with an ion solution. The care composition has a salinity of 0.9%-4% (W/W) and contains less than 0.3% (W/W) of sodium, 0.3%-1% (W/W) of magnesium, and 0.02%-0.2% (W/W) of potassium.

6 Claims, 5 Drawing Sheets

CARE COMPOSITION AND USE THEREOF

CROSS REFERENCE TO RELATED APPLICATIONS

Figure 1:
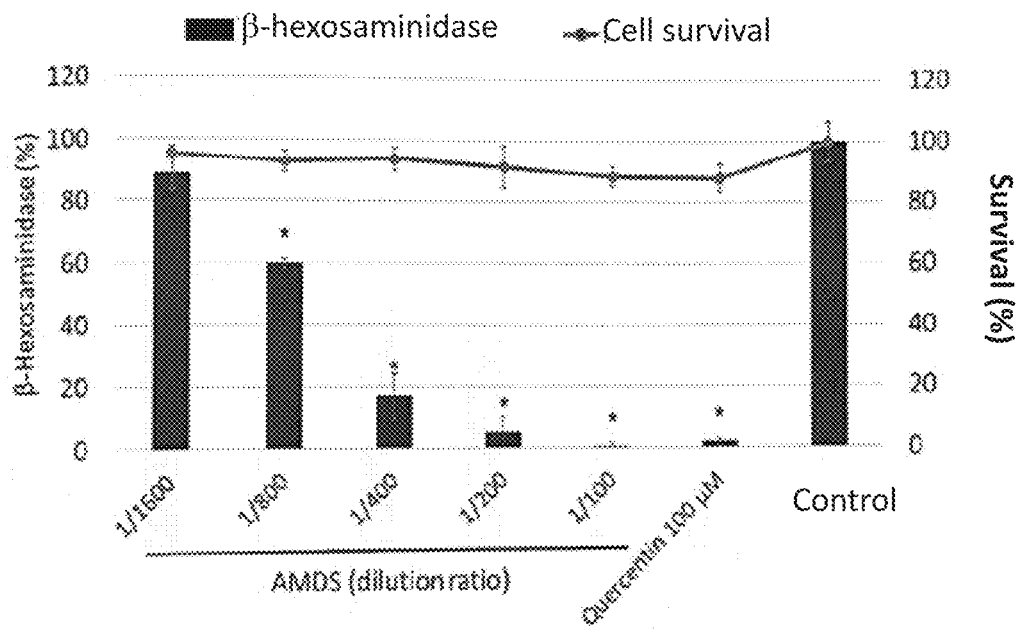

This application claims priority of Taiwan Patent Application No. 109135028, filed on Oct. 8, 2020 under 35 U.S.C. § 119, the entirety of which is incorporated by reference herein.

FIELD OF THE INVENTION

The present invention disclose a care composition and its use thereof, especially regarding the preparation for this care composition, which is related to the methods for regulating the number of the secretory granules in nasal goblet cells.

BACKGROUND OF INVENTION

The mucosa glands of nose, throat, and airway produce approximately 1 to 1.5 liters of thick substance daily. This thick substance is called mucus. The main function of mucus is to capture and to eliminate harmful bacteria and viruses outside of the human bodies, preventing these harmful substances from entering our bodies. Mucus eventually enters the digestive system or be eliminated outside of the human bodies through excretion. The digestion and elimination of the mucus is subtle, similar to that of unconscious movements, for instance winking and breathing. However, when the human body is irritated by viruses or bacteria, these external substances stimulate mucus production, producing more and even thicker mucus. The increased mucus volume and thickness can cause the human body to experience illness; common symptoms are: post nasal drip syndrome (PNDS) and upper airway cough syndrome (UACS) in the airway, blurred vision caused by increased mucus secretion in the eyes, and itchiness and odor caused by increased mucus secretion in the vagina.

Mucus is produced by mucosa. Mucosa includes epithelial cells, goblet cells, and submucosal glands. Goblet cells are located in between mucosal epithelial cells. The apical surface of the goblet cells is exposed to the nasal cavity, this allows the goblet cells to respond rapidly to external harm and invasion, producing even more mucus than the submucosal glands. Therefore, goblet cells play a critical defensing role.

Mucus is a gel-like fluid consists of several compounds, including water and secretions from cells. Mucus is made up of 95% water and of 5% solids. These solid substances include 2-3% proteins and glycoproteins, 1% lipids, 1% salts, and other substances. One of the most important glycoproteins in mucus is the mucin. Mucin also known as mucoprotein, is a polymer consists of proteins and polysaccharides; its oligosaccharide side chains are attached to the peptide core by n-link and o-link glycosylation.

Excessive mucus secretion can cause severe illness in the human bodies and the animal bodies, and can lead to related diseases, such as asthma, chronic obstructive pulmonary disease (COPD), chronic bronchitis, cystic fibrosis, pneumonia, and rhinitis. Flu and common cold can also increase mucus secretion.

To treat the illness caused by excessive mucus secretion, drugs like anti-histamine, corticosteroids, sympathomimetic drugs are often used. However, anti-histamine may cause mucus to thicken, and may cause exacerbation of bacteria caused inflammation. Long-term use of some anti-histamines may develop drug resistance, and the dosage for treatment may increase over time or the types of drugs used may need constant change. Anti-histamine may cause unpleasant side effects, such as headache, dry mouth, dry nose, hypertension, hyperglycemia, cataract, osteoporosis, and endocrine disorders. Corticosteroids and sympathomimetic drugs may also cause side effects, such as dryness, burning, nasal cavity pain, sneezing, and bleeding; sympathomimetic drugs can also cause allergic rhinitis. Treating excessive mucus secretion with treatments listed above for long-term is a great burden to the body.

Goblet cells are recognized as one of the most important defensing factors within the mucosa. Therefore, studies usually determine mucus secretion through measuring goblet cell numbers; however, measuring goblet cell numbers is insufficient to prove the improved regulation of mucus secretion.

SUMMARY OF THE INVENTION

In regard to the complexity of regulating mucus secretion, we need a safe, effective, and burdenless compound to improve the environment in the nasal cavity. The present invention is a care composition related to the regulation of the numbers of secretory granules within the goblet cells, leading to the regulation of mucus secretion.

The present invention provides a care composition is selected from the group consisting of the extract of the stems and/or leaves of a potato, and/or a yam-bean, and/or a yam together with an ion solution containing sodium ion, magnesium ion, and potassium ion.

In one embodiment of the present invention, the salinity of the care composition is 0.9~4%.

In one embodiment of the present invention, the sodium ion content of the care composition is less than 0.3% (W/W).

In one embodiment of the present invention, the magnesium ion content of the care composition is higher than 0.25% (W/W).

In one embodiment of the present invention, the magnesium ion content of the care composition is 0.3~1% (W/W), with magnesium content of 0.3~40.5% (W/W) as the best concentration.

In one embodiment of the present invention, the concentration ratio of magnesium ion to potassium ion in the care composition is 4~17:1 (W/W).

In one embodiment of the present invention, the potassium ion content of the care composition is 0.02~0.2% (W/W).

In one embodiment of the present invention, the ion solution also contains iron, copper, zinc, iodine, chromium, and/or molybdenum.

In one embodiment of the present invention, the care composition is a liquid.

The present invention provides the method for regulation of the secretory granules in nasal goblet cells in a subject, wherein the method comprising administrating to said subject a care composition.

In one embodiment of the present invention, the care composition can regulate the secretion of the secretory granules within the goblet cells.

In one embodiment of the present invention, the care composition is able to degrade histamine.

In one embodiment of the present invention, the care composition is able to inhibit the synthesis of leukotrienes and prostaglandins.

In one embodiment of the present invention, the care composition is able to serve the effects of immunosuppressants, immunomodulators, and anti-inflammatory drugs.

BRIEF DESCRIPTIONS OF THE DRAWINGS

FIG. 1 demonstrates the effect of the care composition of different concentrations on β-hexosaminidase levels. Care composition at dilution rates 1/800, 1/400, 1/200, and 1/100 are able to reduce the levels of β-hexosaminidase.

Figure 2:
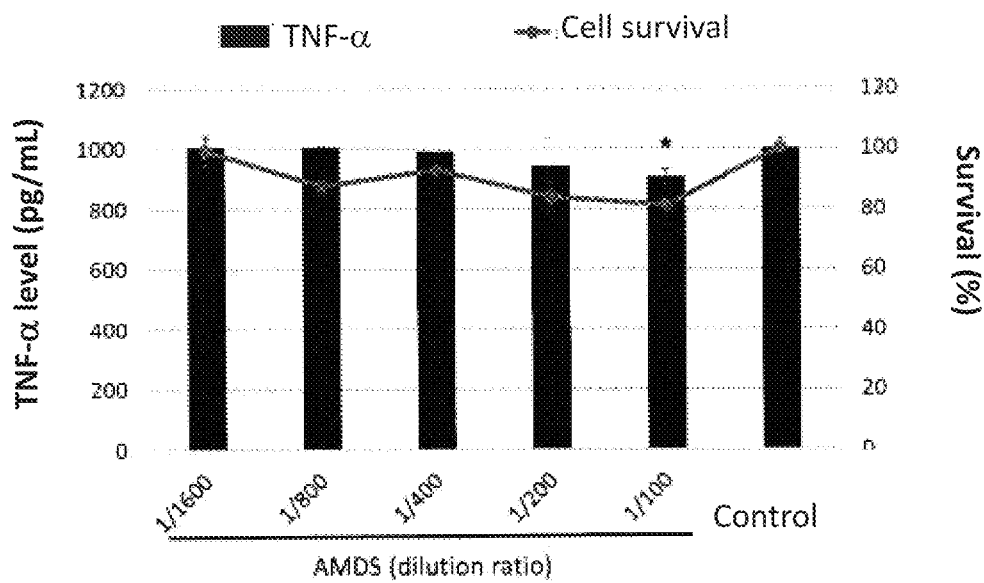

FIG. 2 demonstrates that the care composition at dilution rates 1/200 and 1/100 are able to reduce the levels of tumor necrosis factor-α (TNF-α).

Figure 3:
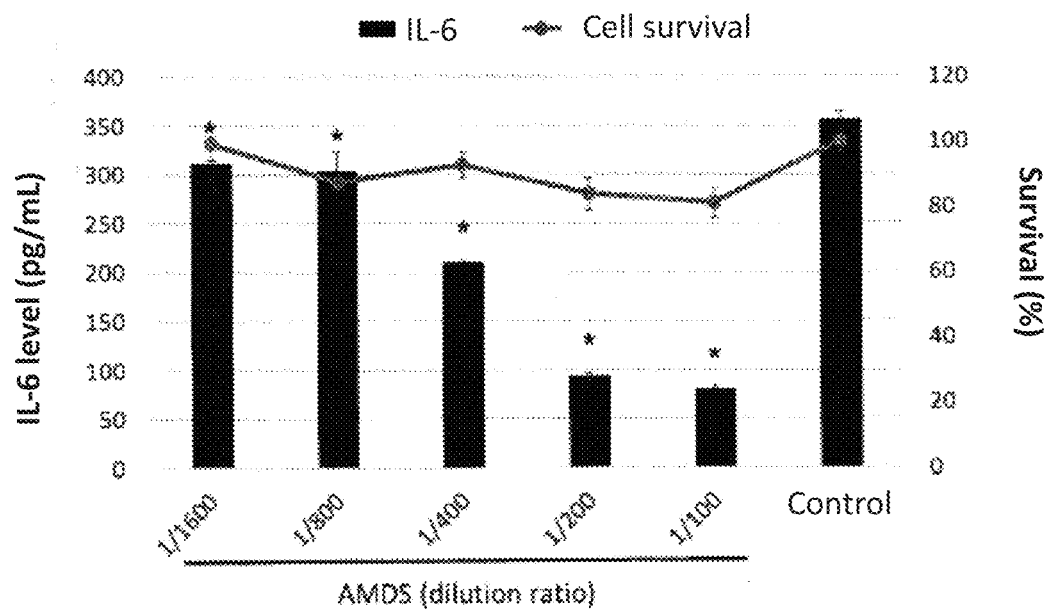

FIG. 3 demonstrates that the care composition at dilution rates 1/1600, 1/800, 1/400, 1/200, and 1/100 are able to reduce the levels of interleukin-6 (IL-6).

Figure 4:
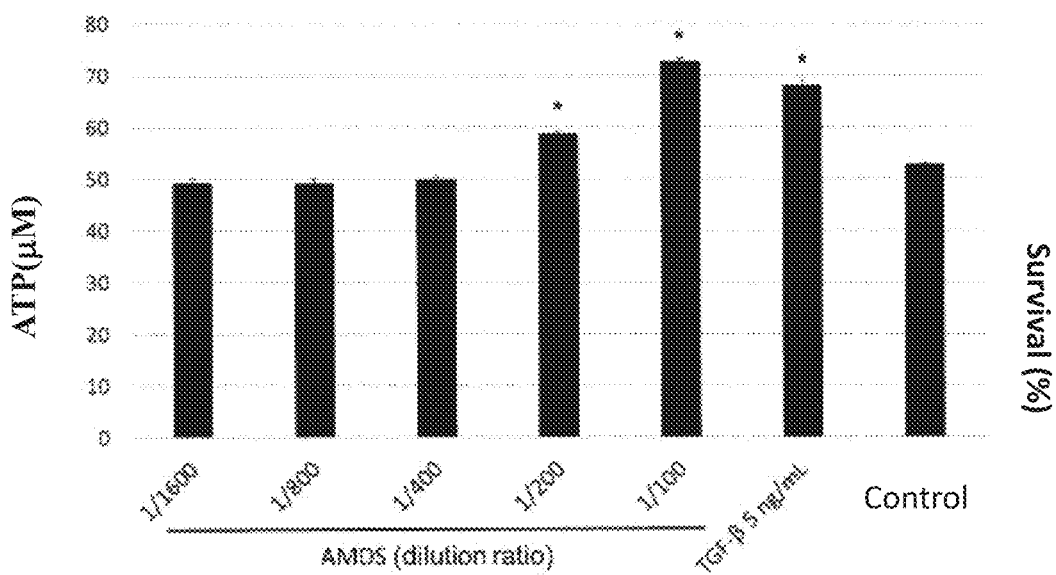

FIG. 4 demonstrates that the care composition at dilution rates 1/200 and 1/100 are able to increase the levels of ATP in cells, providing cells with energy that is needed for anabolism.

Figure 5:
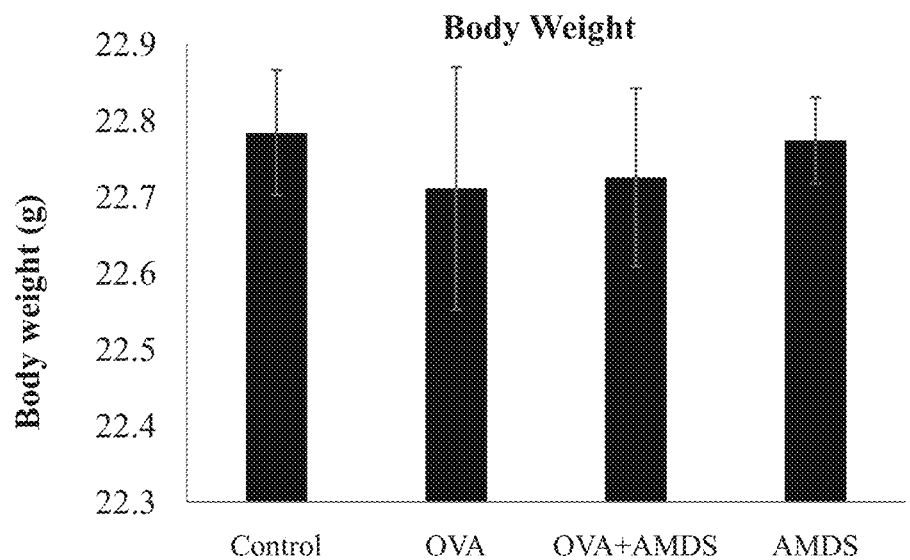

FIG. 5 demonstrates the body weights of the experimental animals.

Figure 6:
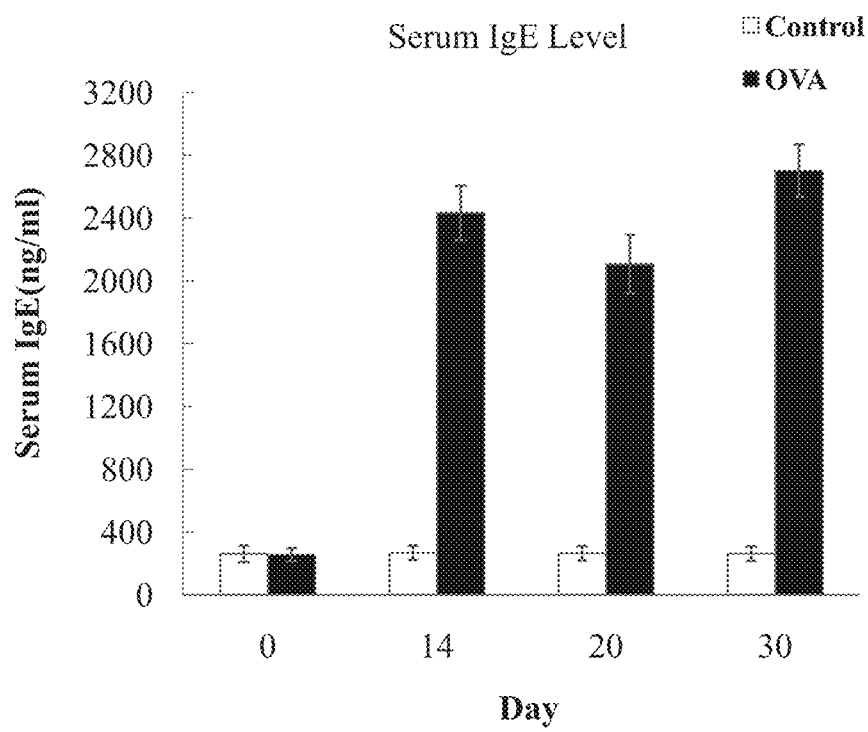

FIG. 6 demonstrates that the serum IgE level significantly increases in ovalbumin-induced (OVA) allergic rhinitis mice.

Figure 7:
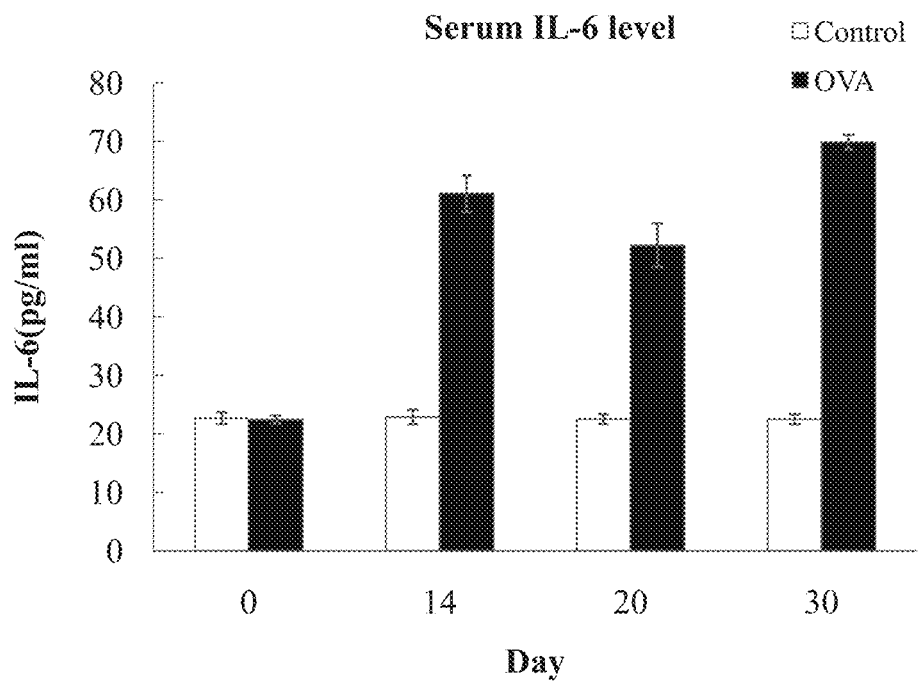

FIG. 7 demonstrates that the serum IL-6 level significantly increases in OVA-induced allergic rhinitis mice.

Figure 8:
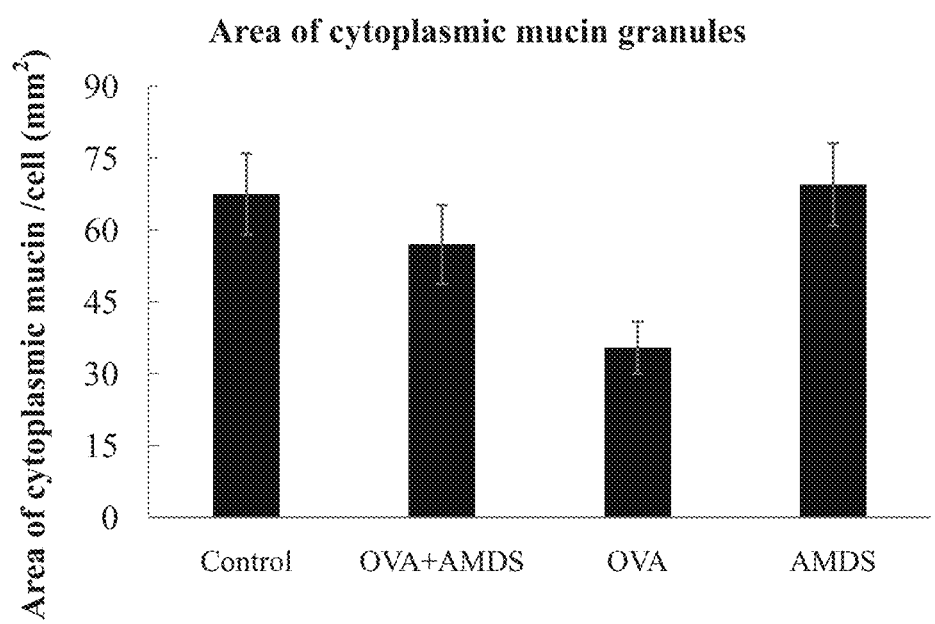

FIG. 8 demonstrates that the PAFS stained area in the goblet cells of the OVA-induced allergic rhinitis mice is 55% less than that of the control mice. The PAFS stained area in the goblet cells of OVA-induced allergic rhinitis mice treated with care composition is only 13% less than that of the control mice. The results indicate that the number of the secretory granules in the goblet cells of OVA-induced allergic rhinitis mice treated with care composition is more than that of the OVA-induced allergic rhinitis mice, and the number of the secretory granules in the goblet cells is similar to that of the control mice.

Figure 9:
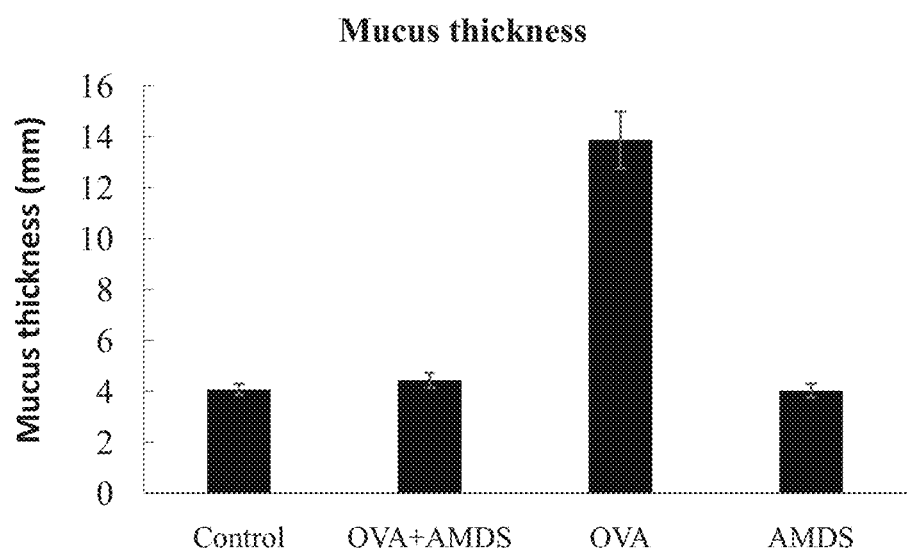

FIG. 9 demonstrates that the percentage increase of the average mucosa thickness in OVA-induced allergic rhinitis mice is 240%, whereas the increase percentage of the average mucosa thickness of those treated with the care composition is only 8%.

DETAILED DESCRIPTION OF THE INVENTION

The present invention provides a care composition made of the stems and/or the leaves of a sweet potato, and/or a yam-bean, and/or a yam, together with an ion solution.

In one embodiments of the care composition, the stems and/or the leaves of a sweet potato, and/or a yam-bean, and/or a yam should be thoroughly cleaned, and tested for residues of chemicals and heavy metals. The inspectors responsible for testing the chemical and heavy metal residues should be familiar with using the liquid chromatography-mass spectrometry (LC/MS), the gas chromatography-mass spectrometry (GC/MS), and other inspection instruments. The stems and/or the leaves used should comply with related regulations.

In one embodiments of the care composition, the stems and/or the leaves of a sweet potato, and/or a yam-bean, and/or a yam are placed in a drying oven, and let dry until the water content is 5~7%. This method allows the water content of the stems and/or the leaves to reduce to 0~10%, for instance, 1%, 2%, 3%, 4%, 5%, 6%, 7%, 8%, 9%, and 10%, the ideal water content is 5~7%.

In one embodiment of the care composition, the dried stems and/or the leaves of a sweet potato, and/or a yam-bean, and/or a yam are ground to the form of powder using a planetary ball mill. In order to maximize the dissolution rate of the ions, the particle size of the powder should be smaller than 1 μm, increasing the contacting area of the powder to the solvent. The particle size of the powder should be between 0.1~5 μm, and the ideal particle size is between 0.1~1 μm.

In one embodiment of the care composition, the magnesium content is greater than 0.25% (W/W), and the concentration ratio of magnesium to potassium is 4~17:1 (W/W).

The concentration of potassium in the extract acquired by using the described extraction method is greater than 50 mg/L, preferably greater than 60 mg/L, for instance, 60 mg/L, 70 mg/L, 80 mg/L, 90 mg/L, 100 mg/L, and 150 mg/L. The ideal potassium concentration is between 65~800 mg/L.

The extract is diluted with electrodialyzed isotonic ion solution (the osmolarity is the same as that of a red blood cell). In one embodiment, the care composition is prepared by mixing the isotonic ion solution, in which the salinity is 0.9% (W/W), with the extract at 1:1 ratio. Within the isotonic ion solution, the concentration of magnesium is 1100~1500 mg/L, the concentration of calcium is 280~390 mg/L, the concentration of potassium is 44~62 mg/L, and the concentration of sodium is 2400~2600 mg/L.

In order to obtain a care composition with specific concentrations of sodium ion, magnesium ion, and potassium ion, the ion solution used to make the care composition has fixed concentration of magnesium, potassium, and sodium. It is to be noted that the care composition is effective with specific concentrations of and ratios between sodium ion, magnesium ion, and potassium ion.

The salinity of the care composition is 0.1~5%, preferably 0.5~2%, and ideally 0.9~4%. The concentration of sodium in the care composition is lower than 3% (W/W), preferably lower than 2%, 1%, 0.9%, 0.8%, 0.7%, 0.6%, 0.5%, 0.4%, 0.3%, 0.2% (W/W), and ideally lower than 0.2%, for instance, 0.1%. Excessive sodium ion in the solution may stimulate the production of pro-inflammatory substances of immune cells, and may reduce ciliary movement, resulting in reduced ability of foreign matter clearance. Therefore, the ideal concentration of sodium should be lower than 0.3% (W/W).

The concentration of magnesium ion in the care composition is greater than 0.3% (W/W), preferably 0.3~1% (W/W), ideally 0.3~0.8% (W/W). The care composition is effective when the concentration of magnesium ion and potassium ion is at a specific ratio; when the proportion of potassium ion is 1, the ideal proportion of magnesium ion is between 1~20, preferably 4~17, for instance, 4, 5, 6, 7, 8, 9, 10, 11, 12, 13, 14, 15, 16, or 17.

In one embodiment of the care composition, the concentration of potassium is 0.02~0.2% (W/W). Sodium ion, magnesium ion and potassium ion play important roles respectively; the concentration of and the ratios between these three ions are critical.

The care composition is able to inhibit the synthesis of pro-inflammatory substances or to aid in the degradation of these substances. The care composition inhibits the levels of pro-inflammatory substances, including, but not limited to, M-CSF, GM-CSF, TNF, IL-1, IL-2, IL-3, IL-4, IL-5, IL-6. IL-7, IL-8, IL-9, IL-10, IL-11, IL-12, IL-13, IL-14, IL-15, IFN, TNF-α, TNF-β, TNF0, TNF1, TNF2, G-CSF, Meg-CSF, NLRP, and/or Caspase.

The care composition is also able to lower the levels of allergy-related substances, including leukotrienes, prostaglandins, histamine, bradykinin, platelet activating factors (PAFs). For instance, magnesium in the care composition aids in the degradation of histamine and inhibits the synthesis of pro-inflammatory substances, such as leukotrienes; potassium, on the other hand, inhibits the synthesis of prostaglandins.

Moreover, the care composition is able to regulate the secretion of mucus. The care composition modulates mucus secretion through regulating the number of secretory granules in goblet cells. The care composition is able to control the secretion of these secretory granules, reducing the secretion of mucus. As a result, the care composition is able to reduce the discomfort symptoms caused by excessive mucus secretion.

The present invention also provides the medical use of the care composition, in regard to the regulation of the number of secretory granules in nasal goblet cells. Persons skilled in the art can make and use the care composition to meet individual needs.

The term 'individual' includes both human and non-human species. Non-human species include companion animals like cats and dogs, and livestock, such as cows, horses, pigs, or sheep.

The care composition is able to reduce and/or to inhibit mucus secretion of the secretory granules in goblet cells. To reduce mucus secretion in target organs, preferably the nasal cavity, drug administration routes recognized in the current state of art can be practiced to deliver the care composition to the secretory granules in the goblet cells of the target organs. Persons skilled in the art understand the procedure of drug delivery, and are capable of combining the care composition with other drug delivery techniques without undue experimentation.

The care composition can be administrated by inhalation (through nasal cavity). The care composition can be made or combined with other medications through current state of the art. Appropriate route of administration is determined by, including but not limited to, the location of the target organ, the features of the disease, the severity of the disease, and the activity of the ingredients. Persons skilled in the art are able to adjust the dosage for administration through a known dosage.

The care composition can be administrated to the airway through any appropriate route. Preferably given as spray consists of inhalable particles. The inhalable particles are comprised of the active ingredients of the care composition. The particles can be in a form of liquid or of solid, and can be combined with other selected therapeutic ingredients. The particle size changes according to the target site, for instances, when given through nasal cavity, the preferred particle size would be 10~500 nm. This allows the active ingredients within the care composition to be combined with suitable agents, such as sterile water, ethanol, isotonic solutions, making the liquid form of the care composition. Commercial sprays can be used to administrate the care composition. The solution or the suspension is transformed into spray by the compression of gases, usually air or oxygen, and the pass-through of a thin micro venturi tube or of an ultrasonicator.

In the present invention, the care composition can be used as the only active ingredient or can be combined with other drugs, for instances immunosuppressants, immunomodulators, or anti-inflammatory drugs. In one embodiment of the present invention, the care composition can be combined with immunosuppressants, immunomodulators, anti-inflammatory drugs, antioxidants, or autophagy activators.

Mucin is the most important ingredient of the mucosa secreted mucus. Mucin is stored within the secretory granules inside goblet cells before secretion. The secretory granules are anchored to the membrane of a goblet cell by Rab protein and Rab effector protein. When the mucosa is stimulated by a foreign stimulus, which signals the secretion of mucus, the G protein and the PLC, located at the inner surface of the goblet cell membrane, produce DAG and IP3; the DAG and IP3 produced activate the subsequent signaling pathways, pulling the secretory granules to the surface of the goblet cell. Mucin in the goblet cell is then secreted by the membrane fusion of the secretory granules and the goblet cell. The released mucin starts absorbing water once it is secreted, expanding the volume of the mucin molecule. Mucin then becomes mucus once it expands to an appropriate volume and also reaches the desirable elasticity and viscosity. When it is unable to block the foreign stimulus, the process of secreting mucus continues, and finally leads to excessive mucus secretion.

Definition

The term 'OVA' used in the present invention represents ovalbumin (OVA).

Embodiment 1

The Preparation and the Making of the Care Composition (A) Drying: The stems and/or the leaves of a sweet potato, and/or a yam-bean, and/or a yam are placed in a 70-degree Celsius drying oven. The stems and/or the leaves, are dried until the moisture content is 5~7% to remove the water and to reduce the activity of organic compounds, preventing the metallic ions from being chelated. (Drying is not applied in general manufacturing process.)

(B) Grinding: in order to maximize the dissolution rate of the ions, the dried stems and/or leaves are placed in a planetary ball mill, and ground to the form of powder with particle size of 1 μm~0.1 μm.

(C) Liquified $CO_2$ is pressurized above critical pressure (>72.9 atm) by using a high-pressure pump. The pressurized $CO_2$ is then injected through a heat exchanger, transforming the $CO_2$ to a supercritical fluid. The supercritical fluid is then injected to a high-pressure tank containing powdered stems and/or leaves of a sweet potato, and/or a yam-bean, and/or a yam. Fat-soluble substances are extracted from the powdered stems and/or leaves of a sweet potato, and/or a yam-bean, and/or a yam by static extraction for 20 minutes and dynamic extraction for 4 minutes. The pressure of the extracted fluid is reduced to 1 atm, and heated to room temperature, vaporizing the $CO_2$. After vaporization, $CO_2$ is then injected into a separating chamber. The $CO_2$ pressure in the separating chamber changes, separating $CO_2$ with fat soluble substances. The $CO_2$ is then recycled through a chiller.

(D) Releasing mineral ions: ion solution (sodium<3000 mg/L, potassium<380 mg/L, magnesium>1100 mg/L, calcium<400 mg/L) is made into an isotonic ion solution through electrodialysis (different from general manufacturing process that uses deionized water). The isotonic solution is then placed into a beaker and bring to boil. Once boiled, add in the dried and ground stems and leaves of sweet potato, and/or yam-bean, and/or yam to the boiled isotonic solution; put a stir-bar into the solution, and cover the beaker with aluminum foil. Let stir for at least an hour at 75-degree Celsius, this process releases the mineral ions from the dried and ground stems and leaves of sweet potato, and/or yam-bean, and/or yam, allowing the magnesium content in the solution to reach above 0.25% (W/W) and the concentration ratio of magnesium to potassium to reach 4~17:1 (W/W).

(E) Precipitation: the solution is cooled down to room temperature. The sodium ion in the solution is removed by injecting carbon dioxide to the solution, forming sodium bicarbonate; the sodium bicarbonate formed is then precipitated, reducing the solution sodium content to less than 0.2% (W/W).

(F) Filtration: to remove the sodium bicarbonate formed, microorganisms, and the residues of the ground stems and leaves of sweet potato, and/or yam-bean, and/or yam, the solution is vacuum filtered through a filter paper (pore size 0.1 μm). The filtered solution is the care composition.

TABLE 1

| Concentration of each ingredient in the care composition | |
|---|---|
| Ingredients | Concentration or ratio |
| Salinity | 0.9~4% |
| Sodium | <0.3% (W/W) |
| Magnesium | 0.25~1% (W/W) |
| Magnesium:Potassium | 4~17:1 (W/W) |

Embodiment 2

Anti-Allergy Effect of the Present Invention

Rat basophilic leukemia cells (RBL-2H3) is seeded in a 96-well cell culture plate, with each well containing $5*10^4$ cells. Cells are incubated in a 37-degree Celsius incubator with 5% $CO_2$ overnight to allow attachment to the culture plate. Replace the culture medium with culture medium containing the care composition (hereinafter referred to as AMDS) of different dilution rates (1/1600, 1/800, 1/400, 1/200, and 1/100) and control groups (a blank control group and a positive control group, which is incubated in culture medium containing quercetin). After 30 minutes of incubation, A23187 (1 μg/mL) is added and allowed reaction for an hour. β-hexosaminidase level is analyzed by applying cell culture supernatant to enzyme-linked immunosorbent assay (ELISA). Replace the culture medium with that containing MTT (0.5 mg/mL), followed with 2-hour incubation. Discard the MTT-medium solution, and add DMSO (150 μL/well) to each well. Let sit in room temperature for 10 minutes, allowing the purple formazan to fully dissolve. The cell survival rate is calculated and determined by detecting the optical density (O.D.) at wavelength 570 in a spectrophotometer.

Cell survival rate (%)=(sample $OD_{570}$/blank control group $OD_{570}$)*100%.

As shown in FIG. 1, AMDS at dilution rates 1/800, 1/400, 1/200, and 1/100 significantly reduces the levels of β-hexosaminidase compared to that of the blank control group. The lower the β-hexosaminidase, the greater the anti-allergy effect. As can be seen in table 2, AMDS has no effect on cell survival (table 2). The results of AMDS inhibiting the synthesis of β-hexosaminidase indicate that AMDS has an anti-allergy effect.

TABLE 2

| Cell survival rate of RBL-2H3 treated with AMDS | | | | | | | |
|---|---|---|---|---|---|---|---|
| | AMDS dilution rate | | | | | Positive control group: | Control: |
| | 1/1600 | 1/800 | 1/400 | 1/200 | 1/100 | quercetin | blank |
| β-hexosaminidase (%) | 88.8 ± 5.23 | 59.7 ± 1.48 | 16.6 ± 7.31 | 5.2 ± 5.16 | 0.4 ± 1.33 | 1.8 ± 1.16 | 100 ± 6.76 |
| Cell survival rate (%) | 95.41 ± 2.16 | 92.9 ± 3.38 | 93.86 ± 3.64 | 91.46 ± 6.58 | 88.48 ± 3.14 | 87.97 ± 4.63 | 100 ± 6.52 |

Embodiment 3

Anti-Inflammatory Effect of the Present Invention.

Mouse macrophage (RAW264.7) is seeded in a 96-well cell culture plate, with each well containing $2*10^2$ cells. Cells are incubated in a 37-degree Celsius incubator with 5% $CO_2$ overnight to allow attachment to the culture plate. Replace the culture medium with culture medium containing AMDS of different dilution rates (1/1600, 1/800, 1/400, 1/200, and 1/100) and a blank control group. Lipopolysaccharide (LPS, 0.1 μg/mL) is added to stimulated cells. After 24 hours of incubation, the TNF-α and IL-6 levels are analyzed by applying cell culture supernatant to ELISA.MTT assay, as described in embodiment 2, is used to determine cell survival rate. As shown in FIG. 2, AMDS at dilution rates 1/200, and 1/100 significantly reduces the levels of TNF-α compared to that of the blank control group (FIG. 2); AMDS at dilution rates 1/1600, 1/800, 1/400, 1/200, and 1/100 significantly reduces the levels of IL-6 compared to that of the blank control group (FIG. 3). As can be seen in table 3, AMDS has no effect on cell survival (table 3). The results of AMDS reducing the levels of TNF-α and IL-6 indicate that AMDS has an anti-inflammatory effect.

TABLE 3

| Cell survival rate of RAW264.7 treated with AMDS | | | | | |
|---|---|---|---|---|---|
| | AMDS dilution rate | | | | | Control: |
| | 1/1600 | 1/800 | 1/400 | 1/200 | 1/100 | blank |
| TNF-α (pg/mL) | 1002.36 ± 29.47 | 1001.39 ± 3.58 | 987.39 ± 1.04 | 937.62 ± 3.31 | 904.63 ± 24.97 | 995.55 ± 24.14 |
| IL-6 (pg/mL) | 310.97 ± 26.87 | 302.71 ± 21.04 | 209.17 ± 2.13 | 93.25 ± 3.96 | 79.76 ± 4.19 | 355.88 ± 7.99 |
| Cell survival rate (%) | 99.38 ± 4.93 | 87.69 ± 2.18 | 92.87 ± 4.13 | 83.87 ± 4.92 | 81.21 ± 4.56 | 100.16 ± 3.23 |

Embodiment 4

Cell Viability Assay

Human fibroblast, Hs68, is seeded in a 6-well cell culture plate, with each well containing $4\times10^5$ cells. Cells are incubated at 37° C. incubator with 5% $CO_2$ overnight to allow attachment to the culture plate. Replace the culture medium with culture medium containing AMDS of different dilution rates (1/1600, 1/800, 1/400, 1/200, and 1/100) and control groups (a blank control group and a positive control group, which is incubated in culture medium containing TGF-β) for 48 hours. Cells are then collected for ATP level analysis, which is carried out by using ATP fluorescence assay.

As shown in FIG. 4, the ATP levels within cells when AMDS is at dilution rates 1/200 and 1/100 are 58.73±0.48 μm and 72.67±0.78 μm, respectively. The ATP level within cell indicates the mitochondria function since mitochondria is responsible for ATP production. When the mitochondria are in poor condition, many signaling pathways in cell are affected, including pathways related to inflammation and immune response. It has been reported that poor or abnormal mitochondria function can cause latened or damage in immune response, leading to reduced defense function of the human body. Since ATP facilitates anabolism, the lower the ATP level, the lesser the synthesis of anti-inflammatory substances. It has also been reported that ATP serves an anti-inflammatory effect. The results show that AMDS increase the level of ATP in cell, indicating that cells are under anabolism, which constructs molecules from smaller ones.

Embodiment 5

Animal Experiments

Forty healthy eight-week-old female BALB/C mice, weighing 23±2 g, are used to established the murine model of allergic rhinitis. The animals are kept under specific-pathogen-free conditions in an animal room at a room temperature of 20~23 degree Celsius, a humidity of 40~60%, and an environment of 12/12 h light/dark cycle. They are fed with an ovalbumin (OVA)-free diet, and have free access to food and water. This allergic rhinitis animal model is induced by intraperitoneal sensitization and by intratracheal challenge of ovalbumin, mimicking the characteristics of allergic rhinitis, including excessive mucus secretion. Mice are divided into four groups, with ten mice in each group (control group: negative control group; OVA group: positive control group; OVA+AMDS group: disease with AMDS treatment group; AMDS group: AMDS treatment group). Allergic rhinitis is induced by intraperitoneal (i.p.) injection of OVA mixed with aluminum hydroxide in saline Q.O.D. from day 0 to day 14; followed by inhalation of OVA and AMDS Q.D. from day 20 to day 29. The mice are sacrificed on day 30. Mice are observed for anthropometry, excretion, and behavior changes, such as olfactory function, nose rubbing and sneezing, daily. Blood samples are collected by tail vein sampling before the first i.p. injection, 10 hours after the last i.p. injection, and before the first inhalation of OVA. Cardiac puncture is used to collect blood samples when sacrifice. The blood samples are analyzed for the levels of IgE and IL-6.

Lungs and tracheae are fixed by using methacarn for paraffin embedment. Fixed tissues are sliced into paraffin sections of 5 mm thickness. After deparaffinization, tissues are stained with periodic acid fluorescent Schiff stain (PAFS). PAFS is a method used to detect polysaccharides in tissues. Since mucin is consist of glycoproteins, which is a conjugation of oligosaccharide chains and protein molecules, PAFS can be used to stain mucin. Through the staining of mucin, secretory granules, which contain mucin, can be observed under a microscope. Three random sections of the tissues are picked for staining in each mouse; ten goblet cells are analyzed in each section. Images are analyzed and quantified by using ImageJ, and data are presented as the average stained area±standard deviation of a single goblet cell.

Throughout the experiment, no significant weight change is observed (FIG. 5). Serum levels of IgE and IL-6 significantly increase in OVA-induced groups, indicating that this allergic rhinitis model is successfully induced (FIG. 6, 7). The mucus in the secretory granules of the goblet cells is the main component of the mucosa. The volume of secreted mucus can be anticipated through the observed number of secretory granules. Release of mucus leads to the reduction of secretory granules in goblet cells, therefore, the more mucus secreted, the less secretory granules observed. PAFS data are shown in FIG. 8. The stained area is analyzed and quantified by using ImageJ. As shown in FIG. 8, within the OVA group, the average stained area in goblet cells is approximately 55% lesser compared to that of the control group; however, when treated with AMDS (OVA+AMDS group), the stained area is only 13% less compared to that of the control group. The results suggest that goblet cells treated with AMDS contain more secretory granules, and the number of the secretory granules is similar to that of the control group.

Moreover, the number of the secretor granules can be used to indicate the volume of secreted mucus. The thickness of the mucosa is analyzed and quantified by using ImageJ. As shown in FIG. 9, the average mucosa thickness in OVA group is 240% greater compared to that of the control group; however, when treated with AMDS, the average thickness is only 8% greater compared to that of the control group.

Taken together, assuming that there are ten goblet cells, with each goblet cell containing only one secretory granule, the total volume of secreted mucus is 10 μl; under the same circumstance of ten goblet cells, with each goblet cell containing five secretory granules, the total volume of secreted mucus would be 50 μl. This explains that mucus secretion is related to the number of secretory granules rather than the number of goblet cells. The care composition, as described in the present state of the art, is able to regulate the number of the secretory granules within the goblet cells, and to modulate mucus secretion.

Since the key to regulating mucus secretion is the number of secretory granules rather than the number of goblet cells. With the same number of goblet cells, reduced mucus secretion is due to reduced number of secretory granules. As can be inferred, regulating the number of goblet cells does not necessarily modulates mucus secretion.

Symbols seen in the results, * represents the p-value between the control group and the experimental groups is <0.05, indicating statistical significance between the control group and the experimental groups. § represents the p-value<0.05 between the OVA group and other groups is <0.05, indicating statistical significance between the OVA group and other groups.

The invention claimed is:

1. A care composition prepared by the following method:
   (1) placing stems and/or a leaves of the sweet potato, a yam-bean, a yam or a combination thereof in a 70-degree Celsius drying oven; and drying until a moisture content is approximately 5-7%, thus preventing organic matters from chelating metallic ions;
   (2) placing the dried stems and/or leaves of the sweet potato, the yam-bean, the yam or the combination thereof in a planetary ball mill, and grinding the dried stems and/or leaves to form powder with a particle size of 0.1 μm-1 μm;
   (3) pressurizing liquified $CO_2$ to above critical pressure (>72.9 atm) by using a high-pressure pump; the pressurized $CO_2$ is then injected through a heat exchanger, transforming the $CO_2$ to a supercritical fluid; the supercritical fluid is then injected to a high-pressure tank containing the powdered stems and/or leaves of the sweet potato, the yam-bean, the yam or the combination thereof, fat-soluble substances are extracted from the powdered stems and/or leaves of the sweet potato, the yam-bean, the yam or the combination thereof by static extraction for 20 minutes and dynamic extraction for 4 minutes, then reducing the pressure of the high-pressure tank to 1 atm and heating of the high-pressure tank to room temperature, vaporizing the $CO_2$ containing the (extracted) fat soluble substances and then injecting the $CO_2$ containing the (extracted) fat soluble substances into a separating chamber, the $CO_2$ and the fat soluble substances are separated in the separating chamber and the $CO_2$ is then recycled through a chiller;
   (4) providing an initial ion solution containing sodium ion, magnesium ion and potassium ion and adjusting the initial ion solution to an isotonic solution through electrodialysis, placing the isotonic solution into a beaker and bringing the isotonic solution to a boil, once boiled, adding in the dried and ground stems and/or leaves of the sweet potato, the yam-bean, the yam or the combination thereof from the step (3) to the boiled isotonic solution; putting a stir-bar into the solution, and covering the beaker with an aluminum foil, stirring for at least an hour at 75-degree Celsius, wherein this process releases mineral ions from the dried and ground stems and/or leaves of the sweet potato, the yam-bean, the yam or the combination thereof, allowing a magnesium ion content in the solution to reach above 0.25% (W/W) and a concentration ratio of magnesium ion to potassium ion to reach 4-17:1 (W/W);
   (5) cooling down the solution obtained from the step (4) to room temperature and reducing the sodium ion content in the solution by injecting carbon dioxide to the solution, forming sodium bicarbonate; precipitating the sodium bicarbonate, thus reducing the solution sodium content to less than 0.3% (W/W); and
   (6) removing the sodium bicarbonate formed and the residues of the ground stems and/or leaves of the sweet potato, the yam-bean, the yam or a combination thereof, by vacuum filtering the solution through a filter paper (pore size 0.1 μm), wherein the filtered solution is the care composition.

2. The care composition of claim 1, wherein a salinity of the care composition is 0.9-4%.

3. The care composition of claim 1, wherein the magnesium ion content is 0.3-1% (W/W).

4. The care composition of claim 1, wherein the potassium ion content is 0.02-0.2% (W/W).

5. The care composition of claim 1, wherein the initial ion solution further contains iron, copper, zinc, iodine, chromium, or molybdenum.

6. A method for regulation of secretory granules in nasal goblet cells in a subject, wherein the method comprises administrating to said subject the care composition of claim 1.

* * * * *